(12) United States Patent
Schaetzl

(10) Patent No.: US 7,387,886 B2
(45) Date of Patent: Jun. 17, 2008

(54) PRION PROTEIN DIMERS USEFUL FOR VACCINATION

(76) Inventor: Hermann Schaetzl, Adelgundenweg 5, 82140 Olching (DE)

( * ) Notice: Subject to any disclaimer, the term of this patent is extended or adjusted under 35 U.S.C. 154(b) by 0 days.

(21) Appl. No.: 10/115,984

(22) Filed: Apr. 5, 2002

(65) Prior Publication Data

US 2002/0168377 A1 Nov. 14, 2002

(30) Foreign Application Priority Data

Apr. 19, 2001 (EP) ................................ 01109707

(51) Int. Cl.
*A61K 39/00* (2006.01)
(52) U.S. Cl. ................... 435/69.3; 424/184; 424/248.1
(58) Field of Classification Search ............... 550/300, 550/350; 536/23.1, 23.4
See application file for complete search history.

(56) References Cited

U.S. PATENT DOCUMENTS

2003/0086938 A1* 5/2003 Jensen et al. ............ 424/185.1

OTHER PUBLICATIONS

Meyer et al. A monomer-dimer equilibrium of a cellular prion protein (PrPC) not observed with recombinant PrP. Journal of Biological Chemistry (2000) vol. 275, No. 48, pp. 38081-38087.*
Burgess et al. Possible dissociation of the heparin-binding and mitogenic activities of heparin-binding growth factor-1 from its receptor-binding activities by site-directed mutagenesis of a single lysine residue. Journal of Cell Biology (1990) vol. 111.*
Korth et al. Monoclonal antibodies specific for the native, disease associated isoform of the prion protein. Methods in Enzymology (1999) vol. 309, pp. 106-122.*
Lazar et al. Transforming growth factor alpha: an aromatic side chain at position 38 is essential for biological activity. Molecular and Cellular Biology (1989) vol. 8, No. 3, pp. 1247-1252.*
Alpha Diagnostic International, Guidelines for anibody production using SDS-gels or gel beads. (1996) pp. 1-2.*
Eurogentec, Polyclonal antibody production.*
Butto et al. Dual infection with different strains of the same HIV-1 subtype. AIDS (1997) vol. 11, No. 5, pp. 694-696.*
Partidos et al. The effect of orientation of epitopes on the immunogenicity of chimeric synthetic peptides representing measles virus protection sequences. Molecular Immunology (1992) vol. 29, No. 5, pp. 651-658, see p. 657, col. 1, 2nd paragraph.*
Tobler et al. Sleep and sleep regulation in normal and prion protein-deficient mice. The Journal of Neuroscience (1997) vol. 17, No. 5, pp. 1869-1879, see introduction and discussion.*
Walz et al. Increased sensitivity to seizure in mice lacking prion protein. Epilepsia (1999) vol. 40, No. 12, pp. 1679-1682.*
Heppner et al. Immunity against prions? Trends in Molecular Medicine (2001) vol. 7, No. 11, pp. 477-479.*
Sigurdason et al. Immunization delays onset of prion disease in mice. American Journal of Pathology (2002) vol. 161, No. 1, pp. 13-17.*
Priola et al. J. Biol. Chem., 1995, vol. 270. p. 3299-3305.*
Veronese et al. IL Pharmaco, 1999, vol. 54, p. 497-516.*
S. A. Priola et al., *J. Biol. Chem.*, vol. 270, No. 7, Feb. 17, 1995 (pp. 3299-3305).
S. Harmeyer et al., *J. General Virol.*, vol. 79, 1998 (pp. 937-945).
Harmeyer et al. "Synthetic Peptide Vaccines Yield Monoclonal Antibodies to Cellular and Pathological Prion Proteins of Ruminants", Journal of General Virology (1998) 79, 937-945.
Munekata et al. "Immunoreactivity of a Synthetic Pentadecapeptide Corresponding to the N-Terminal Region of the Scrapie Prion Protein", Journal of General Virology, (1986) 67, 1745-50.

* cited by examiner

*Primary Examiner*—Bruce R. Campell
*Assistant Examiner*—Agnieszka Boesen
(74) *Attorney, Agent, or Firm*—Crowell & Moring LLP

(57) ABSTRACT

Described is a prion protein, wherein said prion protein is a homodimer or heterodimer. The prion protein dimers are highly immunogenic capable of inducing an immune response in a mammal, thus useful for prophylactic or therapeutic vaccination against diseases associated with the infectious forms of prion proteins, $PrP^{Sc}$, i.e. transmissible spongiform encephalopathies. Moreover, antibodies generated by using the prion protein diners as an antigen, pharmaceutical composition containing the prion protein dimers or antibodies directed against said diners as well as DNA sequences encoding the prion protein diners are described.

10 Claims, 6 Drawing Sheets

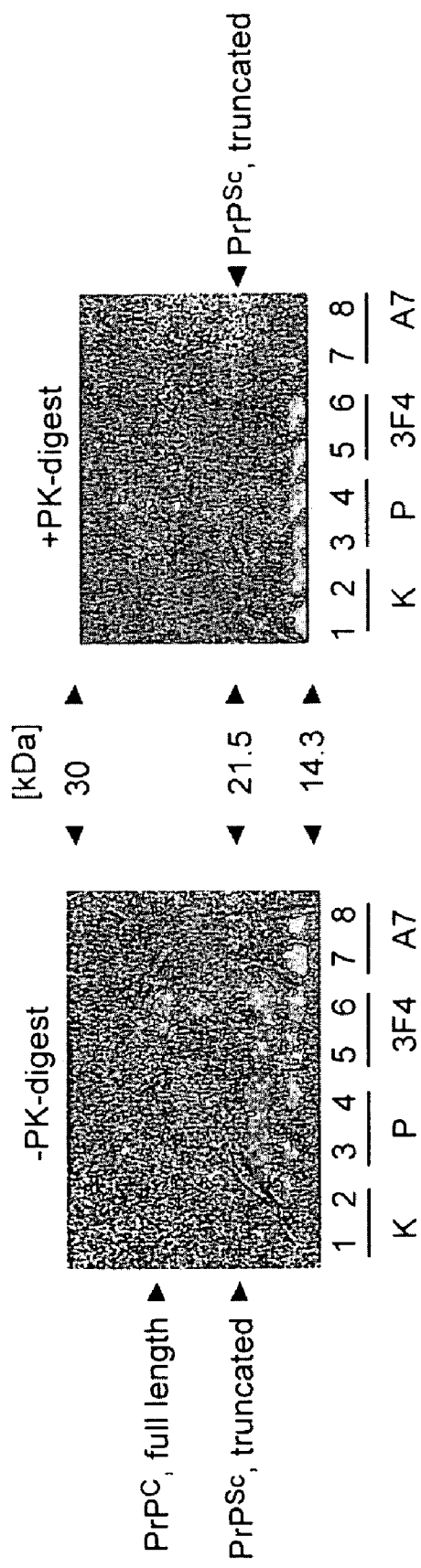

Figure 1:
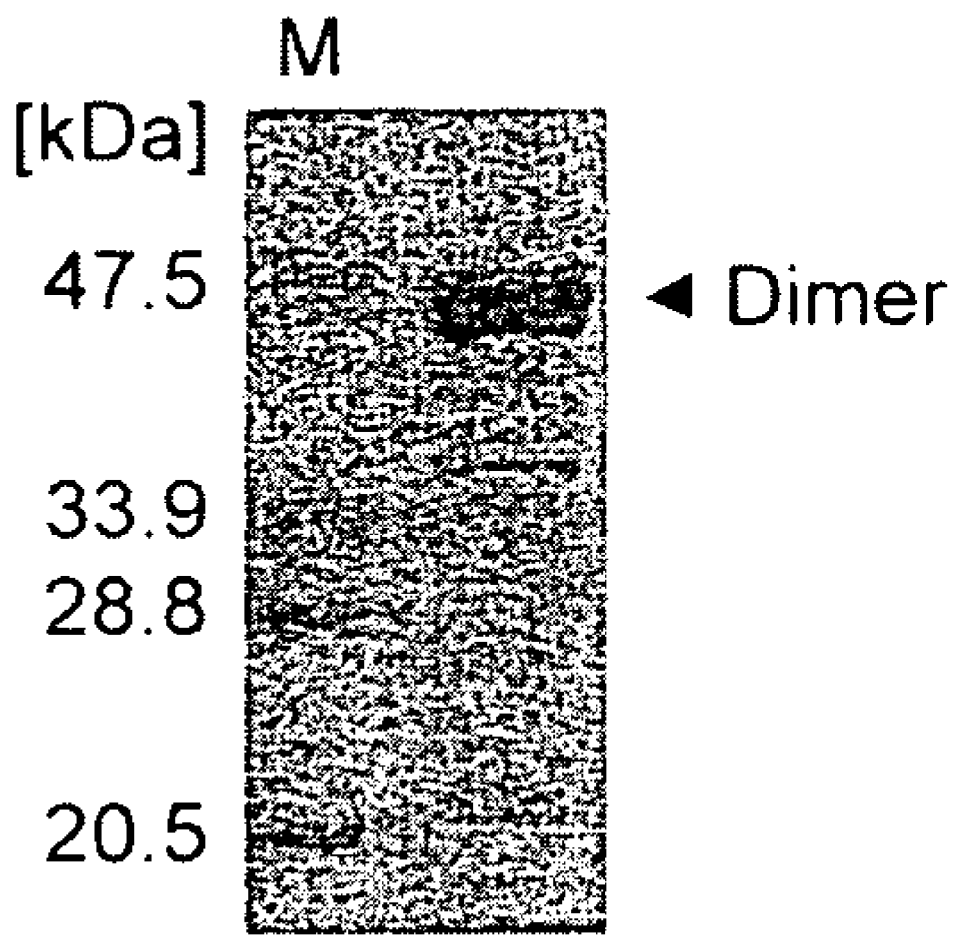

Translation of hisPrPDPcr(1-1320)
Universal code
Total amino acid number: 439, MW=48163
Max ORF: 1-1317, 439 AA, MW=48163

```
1      ATGAGAGGATCGCATCACCATCACCATCACGGATCCTGCAAGAAGCGGCCAAAGCCTGGA
1       M  R  G  S  H  H  H  H  H  H  G  S  C  K  K  R  P  K  P  G

61     GGGTGGAACACTGGCGGAAGCCGATACCCTGGGCAGGGGAGCCCTGGAGGCAACCGTTAC
21      G  W  N  T  G  G  S  R  Y  P  G  Q  G  S  P  G  G  N  R  Y

121    CCACCTCAGGGTGGCACCTGGGGGCAGCCCCACGGTGGTGGCTGGGGACAACCCCATGGG
41      P  P  Q  G  G  T  W  G  Q  P  H  G  G  W  G  Q  P  H  G

181    GGCAGCTGGGGACAACCTCATGGTGGTAGTTGGGGTCAGCCCCATGGCGGTGGATGGGGC
61      G  S  W  G  Q  P  H  G  G  S  W  G  Q  P  H  G  G  G  W  G

241    CAAGGAGGGGGTACCCACAATCAGTGGAACAAGCCCAGTAAGCCAAAAACCAACATGAAG
81      Q  G  G  G  T  H  N  Q  W  N  K  P  S  K  P  K  T  N  M  K

301    CACATGGCCGGCGCTGCTGCGGCAGGGGCCGTGGTGGGGGGCCTTGGTGGCTACATGCTG
101     H  M  A  G  A  A  A  A  G  A  V  V  G  G  L  G  G  Y  M  L

361    GGGAGTGCCATGAGCAGGCCCATGATCCATTTTGGCAACGACTGGGAGGACCGCTACTAC
121     G  S  A  M  S  R  P  M  I  H  F  G  N  D  W  E  D  R  Y  Y

421    CGTGAAAACATGTACCGCTACCCTAACCAAGTGTACTACAGGCCAGTGGATCAGTACAGC
141     R  E  N  M  Y  R  Y  P  N  Q  V  Y  Y  R  P  V  D  Q  Y  S

481    AACCAGAACAACTTCGTGCACGACTGCGTCAATATCACCATCAAGCAGCACACGGTCACC
161     N  Q  N  N  F  V  H  D  C  V  N  I  T  I  K  Q  H  T  V  T

541    ACCACCACCAAGGGGGAGAACTTCACCGAGACCGATGTGAAGATGATGGAGCGCGTGGTG
181     T  T  T  K  G  E  N  F  T  E  T  D  V  K  M  M  E  R  V  V

601    GAGCAGATGTGCGTCACCCAGTACCAGAAGGAGTCCCAGGCCTATTACGACGGGAGAAGA
201     E  Q  M  C  V  T  Q  Y  Q  K  E  S  Q  A  Y  Y  D  G  R  R

661    TCCAGCGCTGGAGCGATCGGTGGAGCTAAAAAGCGGCCAAAGCCTGGAGGGTGGAACACT
221     S  S  A  G  A  I  G  G  A  K  K  R  P  K  P  G  G  W  N  T

721    GGCGGAAGCCGATACCCTGGGCAGGGCAGCCCTGGAGGCAACCGTTACCCACCTCAGGGT
241     G  G  S  R  Y  P  G  Q  G  S  P  G  G  N  R  Y  P  P  Q  G

781    GGCACCTGGGGGCAGCCCCACGGTGGTGGCTGGGGACAACCCCATGGGGGCAGCTGGGGA
261     G  T  W  G  Q  P  H  G  G  G  W  G  Q  P  H  G  G  S  W  G

841    CAACCTCATGGTGGTAGTTGGGGTCAGCCCCATGGCGGTGGATGGGGCCAAGGAGGGGGT
281     Q  P  H  G  G  S  W  G  Q  P  H  G  G  G  W  G  Q  G  G  G

901    ACCCACAATCAGTGGAACAAGCCCAATAAGCCAAAAACCAACATGAAGCACATGGCCGGC
301     T  H  N  Q  W  N  K  P  N  K  P  K  T  N  M  K  H  M  A  G

961    GCTGCTGCGGCAGGGGCCGTGGTGGGGGGCCTTGGTGGCTACATGCTGGGGAGCGCCATG
321     A  A  A  A  G  A  V  V  G  G  L  G  G  Y  M  L  G  S  A  M

1021   AGCAGGCCCATGATCCATTTTGGCAACGACTGGGAGGACCGCTACTACCGTGAAAACATG
341     S  R  P  M  I  H  F  G  N  D  W  E  D  R  Y  Y  R  E  N  M
```

FIG. 5A

```
1081    TACCGCTACCCTAACCAAGTGTACTACAGGCCAGTGGATCAGTACAGCAACCAGAACAAC
361      Y  R  Y  P  N  Q  V  Y  Y  R  P  V  D  Q  Y  S  N  Q  N  N

1141    TTCGTGCACGACTGCGTCAATATCACCATCAAGCAGCACACGGTCACCACCACCACCAAG
381      F  V  H  D  C  V  N  I  T  I  K  Q  H  T  V  T  T  T  T  K

1201    GGGGAGAACTTCACCGAGACCGATGTGAAGATGATGGAGCGCGTGGTGGAGCAGATGTGC
401      G  E  N  F  T  E  T  D  V  K  M  M  E  R  V  V  E  Q  M  C

1261    GTCACCCAGTACCAGAAGGAGTCCCAGGCCTATTACGACGGGAGAAGATCCAGCAGCTAG
421      V  T  Q  Y  Q  K  E  S  Q  A  Y  Y  D  G  R  R  S  S  S  *
```

FIG. 5B

SEQUENCE LISTING

```
<160> NUMBER OF SEQ ID NOS: 15

<210> SEQ ID NO 1
<211> LENGTH: 1320
<212> TYPE: DNA
<213> ORGANISM: Artificial Sequence
<220> FEATURE:
<223> OTHER INFORMATION: Description of Artificial Sequence:
      fusion protein
<220> FEATURE:
<221> NAME/KEY: CDS
<222> LOCATION: (1)..(1317)

<400> SEQUENCE: 1 atg aga gga tcg cat cac cat cac cat cac gga tcc tgc aag aag cgg        48
Met Arg Gly Ser His His His His His His Gly Ser Cys Lys Lys Arg
  1               5                  10                  15 cca aag cct gga ggg tgg aac act ggc gga agc cga tac cct ggg cag        96
Pro Lys Pro Gly Gly Trp Asn Thr Gly Gly Ser Arg Tyr Pro Gly Gln
             20                  25                  30 ggg agc cct gga ggc aac cgt tac cca cct cag ggt ggc acc tgg ggg       144
Gly Ser Pro Gly Gly Asn Arg Tyr Pro Pro Gln Gly Gly Thr Trp Gly
         35                  40                  45 cag ccc cac ggt ggt ggc tgg gga caa ccc cat ggg ggc agc tgg gga       192
Gln Pro His Gly Gly Gly Trp Gly Gln Pro His Gly Gly Ser Trp Gly
     50                  55                  60 caa cct cat ggt ggt agt tgg ggt cag ccc cat ggc ggt gga tgg ggc       240
Gln Pro His Gly Gly Ser Trp Gly Gln Pro His Gly Gly Gly Trp Gly
 65                  70                  75                  80 caa gga ggg ggt acc cac aat cag tgg aac aag ccc agt aag cca aaa       288
Gln Gly Gly Gly Thr His Asn Gln Trp Asn Lys Pro Ser Lys Pro Lys
                 85                  90                  95 acc aac atg aag cac atg gcc ggc gct gct gcg gca ggg gcc gtg gtg       336
Thr Asn Met Lys His Met Ala Gly Ala Ala Ala Ala Gly Ala Val Val
            100                 105                 110 ggg ggc ctt ggt ggc tac atg ctg ggg agt gcc atg agc agg ccc atg       384
Gly Gly Leu Gly Gly Tyr Met Leu Gly Ser Ala Met Ser Arg Pro Met
        115                 120                 125 atc cat ttt ggc aac gac tgg gag gac cgc tac tac cgt gaa aac atg       432
Ile His Phe Gly Asn Asp Trp Glu Asp Arg Tyr Tyr Arg Glu Asn Met
    130                 135                 140 tac cgc tac cct aac caa gtg tac tac agg cca gtg gat cag tac agc       480
Tyr Arg Tyr Pro Asn Gln Val Tyr Tyr Arg Pro Val Asp Gln Tyr Ser
145                 150                 155                 160 aac cag aac aac ttc gtg cac gac tgc gtc aat atc acc atc aag cag       528
```

```
                Asn Gln Asn Asn Phe Val His Asp Cys Val Asn Ile Thr Ile Lys Gln
                                165                 170                 175 cac acg gtc acc acc acc acc aag ggg gag aac ttc acc gag acc gat         576
His Thr Val Thr Thr Thr Thr Lys Gly Glu Asn Phe Thr Glu Thr Asp
            180                 185                 190 gtg aag atg atg gag cgc gtg gtg gag cag atg tgc gtc acc cag tac         624
Val Lys Met Met Glu Arg Val Val Glu Gln Met Cys Val Thr Gln Tyr
        195                 200                 205 cag aag gag tcc cag gcc tat tac gac ggg aga aga tcc agc gct gga         672
Gln Lys Glu Ser Gln Ala Tyr Tyr Asp Gly Arg Arg Ser Ser Ala Gly
    210                 215                 220 gcg atc ggt gga gct aaa aag cgg cca aag cct gga ggg tgg aac act         720
Ala Ile Gly Gly Ala Lys Lys Arg Pro Lys Pro Gly Gly Trp Asn Thr
225                 230                 235                 240 ggc gga agc cga tac cct ggg cag ggc agc cct gga ggc aac cgt tac         768
Gly Gly Ser Arg Tyr Pro Gly Gln Gly Ser Pro Gly Gly Asn Arg Tyr
                245                 250                 255 cca cct cag ggt ggc acc tgg ggg cag ccc cac ggt ggt ggc tgg gga         816
Pro Pro Gln Gly Gly Thr Trp Gly Gln Pro His Gly Gly Gly Trp Gly
            260                 265                 270 caa ccc cat ggg ggc agc tgg gga caa cct cat ggt ggt agt tgg ggt         864
Gln Pro His Gly Gly Ser Trp Gly Gln Pro His Gly Gly Ser Trp Gly
        275                 280                 285 cag ccc cat ggc ggt gga tgg ggc caa gga ggg ggt acc cac aat cag         912
Gln Pro His Gly Gly Gly Trp Gly Gln Gly Gly Gly Thr His Asn Gln
    290                 295                 300 tgg aac aag ccc aat aag cca aaa acc aac atg aag cac atg gcc ggc         960
Trp Asn Lys Pro Asn Lys Pro Lys Thr Asn Met Lys His Met Ala Gly
305                 310                 315                 320 gct gct gcg gca ggg gcc gtg gtg ggg ggc ctt ggt ggc tac atg ctg        1008
Ala Ala Ala Ala Gly Ala Val Val Gly Gly Leu Gly Gly Tyr Met Leu
                325                 330                 335 ggg agc gcc atg agc agg ccc atg atc cat ttt ggc aac gac tgg gag        1056
Gly Ser Ala Met Ser Arg Pro Met Ile His Phe Gly Asn Asp Trp Glu
            340                 345                 350 gac cgc tac tac cgt gaa aac atg tac cgc tac cct aac caa gtg tac        1104
Asp Arg Tyr Tyr Arg Glu Asn Met Tyr Arg Tyr Pro Asn Gln Val Tyr
        355                 360                 365 tac agg cca gtg gat cag tac agc aac cag aac aac ttc gtg cac gac        1152
Tyr Arg Pro Val Asp Gln Tyr Ser Asn Gln Asn Asn Phe Val His Asp
    370                 375                 380 tgc gtc aat atc acc atc aag cag cac acg gtc acc acc acc acc aag        1200
Cys Val Asn Ile Thr Ile Lys Gln His Thr Val Thr Thr Thr Thr Lys
385                 390                 395                 400 ggg gag aac ttc acc gag acc gat gtg aag atg atg gag cgc gtg gtg        1248
Gly Glu Asn Phe Thr Glu Thr Asp Val Lys Met Met Glu Arg Val Val
                405                 410                 415 gag cag atg tgc gtc acc cag tac cag aag gag tcc cag gcc tat tac        1296
Glu Gln Met Cys Val Thr Gln Tyr Gln Lys Glu Ser Gln Ala Tyr Tyr
            420                 425                 430 gac ggg aga aga tcc agc agc tag                                        1320
Asp Gly Arg Arg Ser Ser Ser
        435

<210> SEQ ID NO 2
<211> LENGTH: 439
<212> TYPE: PRT
<213> ORGANISM: Artificial Sequence
<220> FEATURE:
<223> OTHER INFORMATION: Description of Artificial Sequence:
      fusion protein
```

<400> SEQUENCE: 2

```
Met Arg Gly Ser His His His His His His Gly Ser Cys Lys Lys Arg
 1               5                  10                  15
Pro Lys Pro Gly Gly Trp Asn Thr Gly Gly Ser Arg Tyr Pro Gly Gln
             20                  25                  30
Gly Ser Pro Gly Gly Asn Arg Tyr Pro Pro Gln Gly Gly Thr Trp Gly
         35                  40                  45
Gln Pro His Gly Gly Gly Trp Gly Gln Pro His Gly Gly Ser Trp Gly
     50                  55                  60
Gln Pro His Gly Gly Ser Trp Gly Gln Pro His Gly Gly Gly Trp Gly
 65                  70                  75                  80
Gln Gly Gly Gly Thr His Asn Gln Trp Asn Lys Pro Ser Lys Pro Lys
                 85                  90                  95
Thr Asn Met Lys His Met Ala Gly Ala Ala Ala Ala Gly Ala Val Val
             100                 105                 110
Gly Gly Leu Gly Gly Tyr Met Leu Gly Ser Ala Met Ser Arg Pro Met
         115                 120                 125
Ile His Phe Gly Asn Asp Trp Glu Asp Arg Tyr Tyr Arg Glu Asn Met
     130                 135                 140
Tyr Arg Tyr Pro Asn Gln Val Tyr Tyr Arg Pro Val Asp Gln Tyr Ser
145                 150                 155                 160
Asn Gln Asn Asn Phe Val His Asp Cys Val Asn Ile Thr Ile Lys Gln
                 165                 170                 175
His Thr Val Thr Thr Thr Thr Lys Gly Glu Asn Phe Thr Glu Thr Asp
             180                 185                 190
Val Lys Met Met Glu Arg Val Val Glu Gln Met Cys Val Thr Gln Tyr
         195                 200                 205
Gln Lys Glu Ser Gln Ala Tyr Tyr Asp Gly Arg Arg Ser Ser Ala Gly
     210                 215                 220
Ala Ile Gly Gly Ala Lys Lys Arg Pro Lys Pro Gly Gly Trp Asn Thr
225                 230                 235                 240
Gly Gly Ser Arg Tyr Pro Gly Gln Gly Ser Pro Gly Gly Asn Arg Tyr
                 245                 250                 255
Pro Pro Gln Gly Gly Thr Trp Gly Gln Pro His Gly Gly Gly Trp Gly
             260                 265                 270
Gln Pro His Gly Gly Ser Trp Gly Gln Pro His Gly Gly Ser Trp Gly
         275                 280                 285
Gln Pro His Gly Gly Gly Trp Gly Gln Gly Gly Gly Thr His Asn Gln
     290                 295                 300
Trp Asn Lys Pro Asn Lys Pro Lys Thr Asn Met Lys His Met Ala Gly
305                 310                 315                 320
Ala Ala Ala Ala Gly Ala Val Val Gly Gly Leu Gly Gly Tyr Met Leu
                 325                 330                 335
Gly Ser Ala Met Ser Arg Pro Met Ile His Phe Gly Asn Asp Trp Glu
             340                 345                 350
Asp Arg Tyr Tyr Arg Glu Asn Met Tyr Arg Tyr Pro Asn Gln Val Tyr
         355                 360                 365
Tyr Arg Pro Val Asp Gln Tyr Ser Asn Gln Asn Asn Phe Val His Asp
     370                 375                 380
Cys Val Asn Ile Thr Ile Lys Gln His Thr Val Thr Thr Thr Thr Lys
385                 390                 395                 400
Gly Glu Asn Phe Thr Glu Thr Asp Val Lys Met Met Glu Arg Val Val
```

```
                    405                 410                 415
Glu Gln Met Cys Val Thr Gln Tyr Gln Lys Glu Ser Gln Ala Tyr Tyr
            420                 425                 430

Asp Gly Arg Arg Ser Ser Ser
        435

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:
      peptide spacer

<400> SEQUENCE: 3

Ala Gly Ala Ile Gly Gly Ala
                5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:
      peptide spacer

<400> SEQUENCE: 4

Ser Gly Gly Arg Gly Gly
                5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence:
      peptide spacer

<400> SEQUENCE: 5

Gly Ser Gly Gly Gly Gly Ser Gly Gly Gly Gly Ser Gly Gly Ser Gly
                5                   10                  15

Ala

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:
      peptide spacer

<400> SEQUENCE: 6

Gly Gly Gly Gly Ser
                5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:
      peptide spacer

<400> SEQUENCE: 7

Gly Gly Gly Gly Ser Gly Gly Gly Gly Ser
                5                   10
```

```
<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence:
      peptide spacer

<400> SEQUENCE: 8

Gly Gly Gly Gly Ser Gly Gly Gly Gly Ser Gly Gly Gly Gly Ser
                5                  10                  15

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:
      peptide spacer

<400> SEQUENCE: 9

Ala Gly Ala Ile Gly Gly Ala
                5

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:
      Primer

<400> SEQUENCE: 10
gcggatccgt cgccaccatg gcgaaccttg gcta                              34

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence:
      Primer

<400> SEQUENCE: 11
accgatcgct ccagcgctgg atcttctccc gtcgtaat                          38

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence:
      Primer

<400> SEQUENCE: 12
agcgatcggt ggagctaaaa agcggccaaa gcctggag                          38

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence:
      Primer

<400> SEQUENCE: 13
```

-continued

```
atctagatca tcatcatccc acgatcagga aga                                33
```

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:
      Primer

<400> SEQUENCE: 14

```
gatgttggat cctgcaagaa gcggccaaag                                    30
```

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      Primer

<400> SEQUENCE: 15

```
ggaggagatc cagcagctag aagcttttc                                     29
```

PRION PROTEIN DIMERS USEFUL FOR VACCINATION

This application claims priority under 35 U.S.C. §§ 119 and/or 365 EP 01109707.8 filed Europe on 19 Apr. 2001; the entire content of which is hereby incorporated by reference.

The present invention relates to a prion protein, wherein said prion protein is a homodimer or heterodimer. The prion protein dimers are highly immunogenic capable of inducing an immune response in a mammal, thus useful for prophylactic or therapeutic vaccination against diseases associated with the infectious forms of prion proteins, $PrP^{Sc}$, i.e. transmissible spongiform encephalopathies. Furthermore, the present invention relates to antibodies generated by using the prion protein dimers as an antigen, pharmaceutical compositions containing the prion protein dimers or antibodies directed against said dimers as well as DNA sequences encoding the prion protein dimers.

Transmissible spongiform encephalopathies are neurodegenerative diseases such as scrapie of sheep, bovine spongiform encephalopathy (BSE) of cattle and Creutzfeldt-Jakob disease (CJD) of man. Infectious preparations derived from infected brains are resistant to ultraviolet and ionizing radiation as well as other procedures which normally inactivate nucleic acids indicating that nucleic acids are not required for infectivity. Purification of infectious preparations from brains revealed the presence of a protein required for infectivity. These experimental observations led to the "protein only" hypothesis which proposes that particular proteinaceous infectious particles (prions) are responsible for the transmission of transmissible spongiform encephalopathies (Prusiner et al., Proc. Natl. Acad. Sci. USA 95, 13363-13383 (1998)). Prions consist mainly of a protease resistent protein designated $PrP^{Sc}$ (prion protein, "Sc": scrapie), which is an abnormal isoform of the proteinase K sensitive $PrP^C$ ("C":cellular). The prion protein $PrP^C$ is a species specific protein which is physiologically expressed in brain cells and peripheral blood cells as well as, e.g., in spleen. The biological function of $PrP^C$ is so far unknown. Transgenic mice which are no longer capable of expressing $PrP^C$ (PrP knock out mice) do not show any pathological damages and cannot be infected with prions (Bueler et al., Nature 356, 577-582 (1992); Bueler et al., Cell 73, 1339-1347 (1993)).

Both isoforms, $PrP^{Sc}$ and $PrP^C$, share the same amino acid sequence, but differ in their secondary structure. Circular Dichroism (CD) and Fourier Transform Infrared (FTIR) spectroscopy revealed a significantly higher β-sheet content for $PrP^{Sc}$ as compared to a high α-helix content in $PrP^C$. It has been suggested that prion propagation involves the conversion of α-helical domains in $PrP^C$ into β-sheets in $PrP^{Sc}$. The in vitro conversion of $PrP^C$ into a $PrP^{Sc}$-like molecule was demonstrated employing a proteinase K resistance assay.

It has been suggested that for the development of a transmissible spongiform encephalopathy the interaction of $PrP^{Sc}$ and $PrP^C$ is a crucial event, wherein $PrP^{Sc}$ forces a conversion of $PrP^C$ into the pathological conformation ($PrP^{Sc}$) Accordingly, transgenic mice which are no longer capable of expressing $PrP^C$ (PrP knock out mice) are resistant to infections with $PrP^{Sc}$. Although, the prion proteins of various species differ as regards their amino acid sequences, within the group of mammals there is a high homology (88 to 99%). Apparently, due to differences in the amino acid sequences the prion protein cannot be transmitted between certain species (relative or absolute species barrier). Due to the fact that the prion protein is a physiologically expressed protein, each species exhibits immunological tolerance via its own specific prion protein. Unfortunately, so far transmissible spongiform encephalopathies, e.g. BSE, are incurable. There is no therapy available for soothing the symptoms of the disease, let alone for stopping the disease, e.g. by vaccination.

Therefore, it is the object of the present invention to provide a vaccine for the prevention or treatment of a transmissible spongiform encephalopathy.

According to the invention this is achieved by the subject matters defined in the claims.

The present invention provides a prion protein, wherein said prion protein is a homodimer or heterodimer with the monomer corresponding to or comprising a prion protein according to the definition below. During the experiments leading to the present invention, it has, surprisingly, been found that prion protein dimers are useful for inducing an enhanced immune response against $PrP^c$ and $PrP^{Sc}$. Using this apparent remarkable immunogenicity of the prion protein dimer it was even possible in vivo to generate antibodies directed against the homologous prion protein (i.e. mouse antibodies directed against murine PrP), thereby abolishing or by-passing the known anto-tolerance present within a given species. After incubation of cells permanently producing $PrP^{Sc}$ with the antibodies that were generated by immunization with the prion protein dimer for 16 hours a drastic inhibition of the de novo synthesis of $PrP^{Sc}$ could be observed. Presumably, this result is due to generation of a functional $PrP^c$ knock out state where the surface-located $PrP^c$ substrate needed for continuous cellular conversion into $PrP^{sc}$ is functionally impaired, resulting finally in inhibition of generation of $PrP^{sc}$. It is known from the literature that the surface location of $PrP^c$ is a prerequisite for cellular prion conversion (Taraboulos et al., J. Cell Biol. 129, 121-132 (1995)). Even more, studies with transgenic mice have demonstrated that peripheral expression of $PrP^c$ is absolutely required for replication and transport of $PrP^{sc}$ from peripheral sites of the body to the central nervous system (Blättler et al., Nature 389, 69-73 (1997)). In this respect it has been discovered by the inventors that after application of the prion protein dimer of the present application to a subject, the induced immune response results in the downregulation of the surface expression of $PrP^c$. Accordingly, the conversion rate ($PrP^c \Rightarrow PrP^{Sc}$) can be drastically reduced, thus, blocking the initiation and the progression of the disease. Thus, the prion protein dimers of the present invention are useful as a vaccine for the prevention or treatment of a transmissible spongiform encephalopathy.

Accordingly, the present invention relates to a prion protein, wherein said prion protein is a homodimer or heterodimer which can elicit an immune response against $PrP^C$ or $PrP^{Sc}$, preferably an immune response which is higher compared to the immune response obtained using for vaccination the corresponding monomer. As used herein, the term "prion protein" comprises the native (full length and/or mature) protein as well as variants thereof, e.g. truncated versions, which are still useful for eliciting an enhanced immune response, i.e. still useful for vaccination. In this context, the term "protein" also comprises peptides or polypeptides having a length of at least 8, preferably of at least 15 and, more preferably, of at least 20 amino acids. The person skilled in the art knows sources for the prion protein monomers and DNA sequences encoding the prion protein monomers, respectively (Schätzl et al., J. Mol. Biol. 245, 362-374 (1995); Wopfner et al., J. Mol. Biol. 289, 1163-1178 (1999); sequences deposited at Genbank accessible via Public Medline database). Furthermore, a person skilled in the art knows methods for coupling the monomers in order to obtain the dimer. Preferably, the monomers are covalently coupled.

In a preferred embodiment, the homodimer or heterodimer is a fusion protein comprising the monomeric prion protein units. Such a fusion protein can be generated by methods well known by the person skilled in the art. The selection of a particular method mainly depends on the length of the monomers, i.e. very short fusion proteins are preferably chemically synthesized, e.g. by standard solid phase synthesis, whereas longer fusion proteins are preferably produced by expression of the corresponding DNA sequences in a suitable host and isolation/purification of the fusion protein from the host or the culture medium.

Generally, by means of conventional molecular biological processes (see, e.g., Sambrook et al., 1989, Molecular Cloning, A Laboratory Manual, $2^{nd}$ edition Cold Spring Harbor Laboratory Press, Cold Spring Harbor, N.Y.) it is not only possible to generate a DNA sequence encoding the desired fusion protein but, additionally, to introduce different mutations into the DNA sequence. One possibility is the production of deletion mutants in which DNA molecules are produced by continuous deletions from the 5'- or 3'-termini of the coding DNA sequence and that lead to the synthesis of proteins that are shortened accordingly. The person skilled in the art can easily check as to whether such prion protein diners containing shortened monomeric units are still useful as a vaccine, e.g. using the methods described in the examples, below. For the manipulation in prokaryotic cells by means of genetic engineering the DNA sequences can be introduced into plasmids allowing a mutagenesis or a modification of a sequence by recombination of DNA sequences. By means of conventional methods (cf. Sambrook et al., 1989, Molecular Cloning: A Laboratory Manual, $2^{nd}$ edition, Cold Spring Harbor Laboratory Press, N.Y., USA) bases can be exchanged and natural or synthetic sequences can be added. Furthermore, manipulations can be performed that provide suitable cleavage sites or that remove superfluous DNA or cleavage sites. If insertions, deletions or substitutions are possible, in vitro mutagenesis, primer repair, restriction or ligation can be performed. As analysis method usually sequence analysis, restriction analysis and other biochemical or molecular biological methods are used.

In a more preferred embodiment, the monomers of the fusion protein are linked via a peptide spacer. Suitable peptide spacers, which preferably consist of non-polar and non-bulky amino acids, have a length below 20 residues, provide a certain flexibility, thereby avoiding e.g. cystein or prolin residues which can induce rigidity (or vice versa in cases when rigidity or induction of an orientation/turns are wanted). These spacers are known to the person skilled in the art and comprise for example AGAIGGA [HIV-1 protease; Kräusslich et al., Proc. Natl. Acad. Sci. USA, 88, 3212-3217 (1991)], SGGRGG [HIV gp41; Tan et al., Proc. Natl. Acad. Sci USA, 94, 12303-12308 (1991)], GSGGGGSGGGGSGGSGA [single chain T-cell receptor; Khandekar et al., J. Biol. Chem. 272, 32190-32197 (1997)] or $(GGGGS)_{n=1-3}$ [single chain antibodies; Kortt et al., Eur. J. Biochem. 221, 151-157 (1994)]. Examples of preferred spacers are (a) spacers having a length of 2 to 3 amino acids, wherein the DNA sequence encoding said spacer contains a restriction site, (b) oligomers composed of small neutral amino acids (e.g. Ala-Gly-Ala-Ile-Gly-Gly-Ala), or c) an oligomer having an amino acid sequence that defines an epitope, e.g. flag-tag, HA-epitope etc. . . .

For the generation of the prion protein dimers encoding DNA sequences and for constructing expression vectors which contain said DNA sequences, it is possible to use general methods known in the art. These methods include e.g. in vitro recombination techniques, synthetic methods and in vivo recombination methods as described in Sambrook et al., Molecular Cloning, A Laboratory Manual, $2^{nd}$ edition (1989) Cold Spring Harbor Laboratory Press, Cold Spring Harbor, N.Y., for example.

For recombinant production of the dimeric prion protein of the invention, the DNA sequences encoding said protein are inserted into a suitable expression vector. Preferably, they are plasmids, cosmids, viruses, bacteriophages and other expression vectors usually used in the field of genetic engineering. Expression vectors suitable for use in the present invention include, but are not limited to e.g. pGEMEX, pUC derivatives, pGEX-2T, pET3b, T7 based expression vectors and pQE and pTrcHis (for expression in *E.coli*). For the expression in yeast, e.g. pY100 and Ycpad1 have to be mentioned while e.g. pcDNA3.1, pKCR, pEFBOS, cDM8, pMSCND, and pCEV4 have to be indicated for the expression in animal cells. The baculovirus expression vector pAcSGHisNT-A is especially suitable for the expression in insect cells. The DNA sequences can also be contained in a recombinant virus containing appropriate expression cassettes. Suitable viruses that may be used in the present invention include baculovirus, SFV, vaccinia, sindbis virus, SV40, Sendai virus, adenovirus, an AAV virus or a parvovirus, such as MVM or H-1. The vector may also be a retrovirus, such as MOMULV, MoMuLV, HaMuSV, MuMTV, RSV or GaLV. Preferably, the DNA sequence is operatively linked to the regulatory elements in the recombinant vector that guarantee the transcription and synthesis of an RNA in prokaryotic and/or eukaryotic cells that can be translated. The nucleotide sequence to be transcribed can be operably linked to a promoter like a T7, metallothionein I or polyhedrin promoter. For expression in mammals, the DNA sequences are operatively linked to a suitable promoter like, e.g. a human cytomegalovirus “immediate early promoter” (pCMV).

Suitable host cells include bacteria, yeast, insect and animal cells, preferably mammalian cells. The *E. coli* strains HB101, DH1, x1776, JM101, JM109, BL21, XL1Blue and SG 13009, the yeast strain Saccharomyces cerevisiae, the insect cells sf9 and the animal cells L, A9, 3T3, FM3A, BHK, human SW13, CHO, COS, Vero and HeLa are preferred. Methods of transforming these host cells, of phenotypically selecting transformants and of expressing the DNA according to the invention by using the above described vectors are known in the art. For recombinant production of the dimeric prion protein of the invention, the host cell is cultivated under conditions allowing the synthesis of the protein and the protein is subsequently isolated from the cultivated cells and/or the culture medium. Isolation and purification of the recombinantly produced proteins may be carried out by conventional means including preparative chromatography and immunological separations involving affinity chromatography with monoclonal or polyclonal antibodies, e.g. with the antibody A7 and 3F4 described in the examples, below.

In an alternative preferred embodiment the monomers of the dimeric prion protein of the invention are covalently coupled via suitable compounds, e.g. in such a way that the monomers are covalently linked via their C-termini or N-termini or via the C-terminus of one monomer and the N-terminus of the other monomer. Care has to be taken that dimerization is carried out in such a way that eliciting an immune response by the dimeric protein is not adversely effected. Suitable compounds for dimerization are known to the person skilled in the art, preferably such a compound is a polyethylenglycole, activated benzodiazepine, oxazolone, aminimide, azalactone, diketopiperazine or a monosaccharide. The corresponding chemical reactions are also known to the person skilled in the art.

The monomers of the dimeric prion protein of the present invention can be identical (homodimer: the monomers are derived from the same species) or different (heterodimer: the monomers are derived from different species). In the case of the heterodimer it can be expected that an immune response against the own $PrP^C$ as well as the foreign $PrP^C$ is induced.

As already described above the dimeric prion protein of the present invention also includes monomers which are variants of the native prion protein monomers. Particularly preferred are variants which are N-terminally and/or C-terminally truncated proteins (monomers).

A preferred dimeric prion protein (and its corresponding nucleotide sequence) is shown in FIG. 5.

The present invention also relates to the use of a dimeric prion protein of the present invention for the production of polyclonal or monoclonal antibodies as well as to an antibody, preferably a monoclonal antibody which binds to the dimeric prion protein of the present invention. Such antibodies are useful for passive immunization and can be produced according to well known methods. The term "antibody", preferably, relates to antibodies which consist essentially of pooled monoclonal antibodies with different epitopic specificities, as well as distinct monoclonal antibody preparations. Monoclonal antibodies are made using as an antigen the dimeric prion protein of the invention by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316-325 (1983).) Thus, these fragments are preferred, as well as the products of a FAB or other immunoglobulin expression library. Moreover, antibodies of the present invention include chimeric, single chain (scFv), and humanized antibodies.

Moreover, the present invention also relates to DNA sequences encoding the dimeric prion proteins of the present invention as well as an expression vector containing such a DNA sequence. Examples of such DNA sequences and suitable expression vectors are already described above. Such DNA sequences or expression vectors are not only useful for the recombinant production of the dimeric prion protein of the present invention but also useful as "genetic vaccine". For the preparation of a genetic vaccine, the DNA sequences of the invention are inserted into an appropriate vector under the control of a suitable promoter, e.g. a vector or promoter as described above. Additional suitable vectors are, e.g., herpes simplex virus type 1 amplicon or recombinant Semliki forest virus vectors, plus-strand RNA virus vectors (lentiviral vectors), minus-strand RNA virus vectors (e.g. Rabies virus, RSV). In this connection also "gene gun" applications are suitable. A vaccine according to the present invention can be used to stimulate humoral and/or cellular immune response in subjects who may benefit from such responses by protection against or treatment of a transmissible spongiform encephalopathy.

Finally, the present invention relates to a pharmaceutical composition comprising a dimeric prion protein, an antibody, DNA sequence or an expression vector of the present invention in a pharmaceutically acceptable carrier. After application to the subject, the immune response induced should result in the downregulation of the surface expression of $PrP^C$. Accordingly, the transport of infectious prions from peripheral sites of inoculation (e.g. oral or i.v.) to the central nervous system as well as the initial peripheral replication should be significantly impaired. In addition, the conversion rate ($PrP^C \Rightarrow PrP^{Sc}$) can be drastically reduced, thus blocking the progression of the disease. Thus, the compounds of the present invention are useful for the preparation of a vaccine for the prevention or treatment of a transmissible spongiform encephalopathy (prophylactic or therapeutic vaccination). For the preparation of the vaccine the purified compounds described above may be combined with any suitable adjuvant such as ISCOMS, alum, Freund's Incomplete or Complete Adjuvant, Quil A and other saponins or any other adjuvant as described in the literature. Suitable doses and routes of administration depend on the particular compound and are well known to the person skilled in the art.

BRIEF DESCRIPTION OF THE DRAWINGS

FIG. 1: PrP dimer

Coomassie blue staining after purification showing a purity of >90%. M, molecular weight standards.

FIG. 2: Characterization of the PrP dimer using CD

The results show that the PrP monomer and the PrP dimer have a similar or even identical secondary structure.

FIG. 3

(a) Immunological responses in different mice

Immunization with the PrP monomer and PrP dimer, respectively. Recombinant murine PrP was separated on a SDS PAGE gel, subsequently transferred to a PVDF membrane and the immunoblots were probed with decreasing concentrations auf mice antisera. The immunization with the PrP dimer resulted in an enhanced antibody production.

(b) Immunological responses in different rabbits

Immunization with the PrP monomer and PrP dimer, respectively. Recombinant PrP monomer ($PrP_M$) and PrP dimer ($PrP_D$), respectively, were separated on a SDS PAGE gel, subsequently transferred to a PVDF membrane and the immunoblots were probed with anti-$PrP_{monomer}$ and anti-$PrP_{dimer}$, respectively. The immunization with the PrP dimer resulted in an enhanced antibody production.

FIG. 4: In vitro experiments using $PrP^{Sc}$ infected cells

During incubation with antibodies for 16 hours proteins were metabolically labeled using $^{35}$S-methionine and subsequently immunoprecipitated (RIPA). Prior to the RIPA the cell lysates were separated into two fractions for digestion with proteinase K (+/−) and separated into soluble and insoluble fractions using ultracentrifugation (1 hour, 100,000×g, 1% sarcosyl); data only shown for the insoluble fraction. Only after incubation with A7 a drastic decrease of the de novo synthesis of $PrP^{Sc}$ can be observed. A,B: after deglycosylation using PNGase F; K: without incubation with antibodies; P: preimmune serum; 3F4: monoclonal antibody directed against the 3F4 epitope of the prion protein; A7: antibody obtained from rabbits which had been immunized with the PrP dimer.

FIG. 5: Translation of hisPrPDPcr (1-1320)

Underlined in the first line: His-Tag

Underlined in the middle: Linker

The present invention is explained by the examples.

EXAMPLE 1

Figure 2:
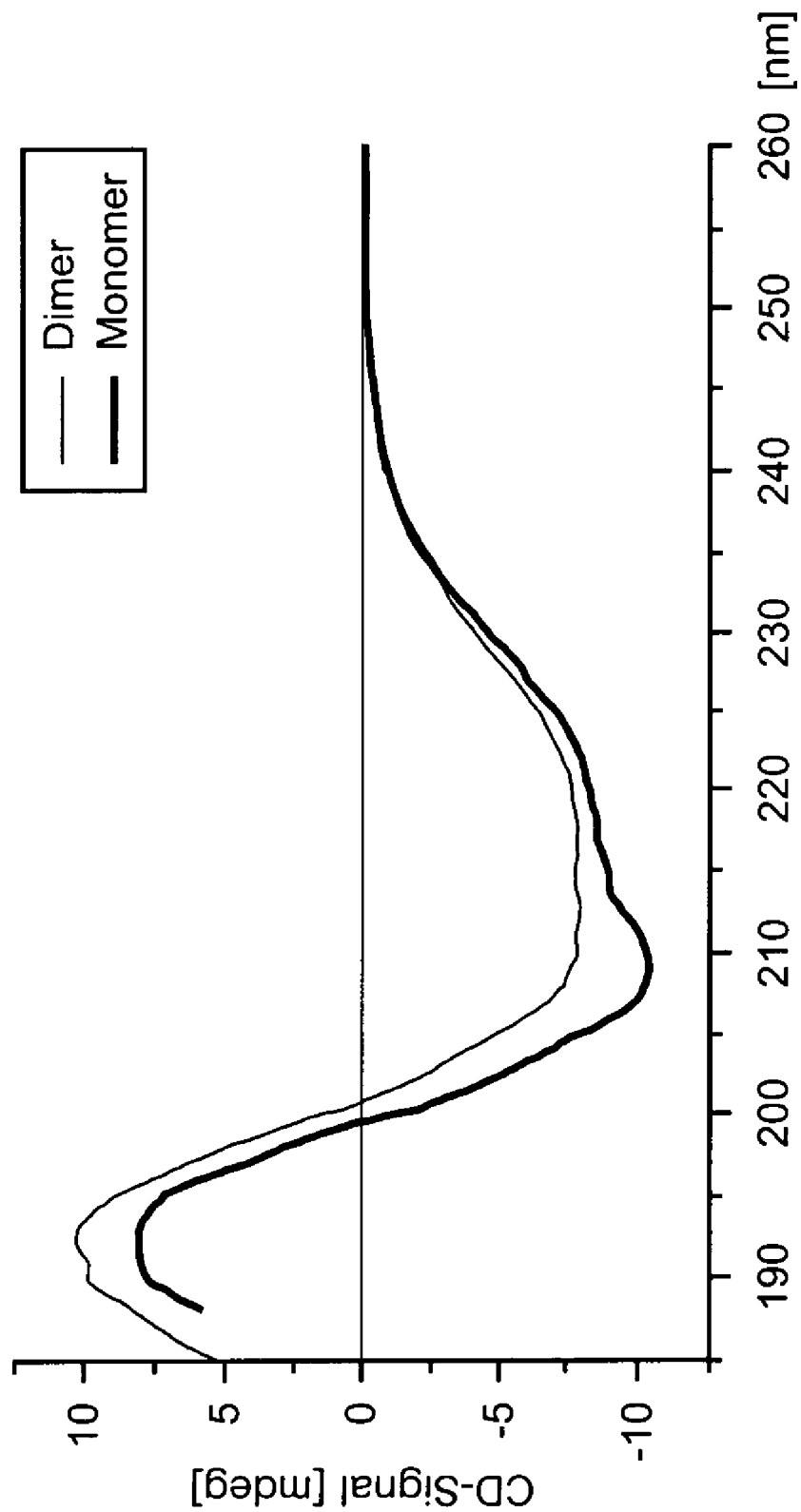

Generation of a Fusion Protein (Dimer) Comprising Two Prion Protein Monomers Covalently Linked by a Peptide Linker Mouse genomic DNA encoding the prion protein (murine PrP-A, derived from murine N2a neuroblastoma cell line; for sequence see Schätzl et al, 1995, supra; Wopfner et al., 1999, supra) was amplified by polymerase chain reaction (PCR) using the following primer pairs which introduce a peptide linker (Ala-Gly-Ala-Ile-Gly-Gly-Ala) encoding sequence containing a PvuI restriction site; primer pair I: 5'-GCG GAT CCG TCG CCA CCA TGG CGA ACC TTG GCT A-3' (PrPB+1) and 5'-ACC GAT CGC TCC AGC GCT GGA TCT TCT CCC GTC GTA AT-3' (231+L new); primer pair II: 5'-AGC GAT CGG TGG AGC TAA AAA GCG GCC AAA GCC TGG AG-3' (23+L new); 5'-ATC TAG ATC ATC ATC ATC CCA CGA TCA GGA AGA-3' (254 PX) (the DNA sequence encoding the PvuI restriction site is underlined). For the introduction of an N-terminal His-tag, the removal of the N-terminal and C-terminal signal peptides and the introduction of additional restriction sites, a second PCR was carried out using the following primers: 5'-GAT GTT GGA TCC TGC AAG AAG CGG CCA AAG-3' (5'-primer, the BamHI-site is underlined.); 5'-GGA GGA GAT CCA GCA GCT AGA AGC TTT TC-3' (3'-primer, the HindIII-site is underlined.) The PCR fragment obtained (c.f. FIG. 5) was inserted into the pQE30 expression vector (Qiagen, Hilden, Del.). In order to obtain higher yields of the recombinantly produced protein, proteinase deficient bacteria (BL21, Stratagene Europe, Amsterdam, The Netherlands) were used for expression. Four hours after induction of expression using 2 mM IPTG, bacteria were lysed in 6 M guanidine hydrochloride (6 M guanidine hydrochloride, 20 mM sodium phosphate, 500 mM sodium chloride, pH 7,8). cell debris were pelleted by centrifugation (20 min., 10,000× g), the supernatant was loaded on a $Ni^{2+}$loaded SP-HiTrap column (Amersham Pharmacia, Uppsala, Sweden) which had been previously equilibrated using binding buffer (8 M urea, 20 mM sodium phosphate, 500 mM sodium chloride, pH 7.8) and incubated. The column was washed for several times (8 M urea, 20 mM sodium phosphate, 500 mM sodium chloride, 80 mM imidazole, pH 6.3) and, subsequently, the fusion protein containing the His-tag was eluted using 8 M urea, 20 mM sodium phosphate, 500 mM sodium chloride, 500 mM imidazole, pH 6.3. Fractions of the eluate were collected. The fractions showing the highest protein concentration were pooled and for removal of urea dialyzed against pure water (Slide-A-Lyzer, Pierce, Bonn, Del.). As shown in FIG. 1, the protein could be obtained with a very high purity. As shown in FIG. 2, the secondary structure of the purified renatured dimer is similar (or even identical) to the secondary structure of the prion protein monomer.

EXAMPLE 2

Immunization of Mice and Rabbits

Figure 3A:
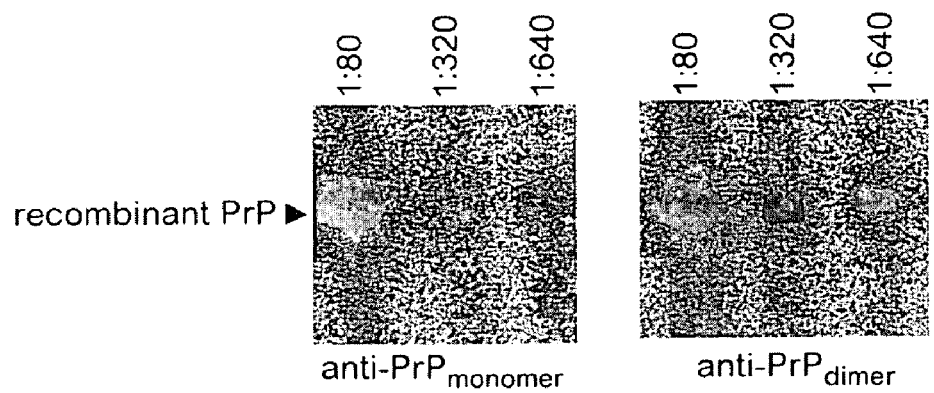

Ten female $B6D_2F_1$ (B57BL/6×DBA) mice (inbred strain generated at the Institute of Molecular Animal Breeding/Gene Center Munich, Del.; six weeks old) were immunized by subcutaneous injections of 50 μg of the protein dimer described in Example 1 and a control monomer, respectively (monomer: murine PrP23-231 verus dimer: murine PrP23-231=23-231 [connected by the linker sequence], both with the 3F4 epitope and an N-terminal poly-histidine tag). At day 0 the proteins were combined with Freund's Complete Adjuvant, for boostering (at day 21 and day 42, respectively) the proteins were combined with Freund's Incomplete Adjuvant. Ten days after the last immunization blood samples for antibody evaluation were taken. It could be shown that the application of the prion protein monomer (control) resulted in the generation of a lower amount of specific antibodies compared to the application of the prion protein diner. After application of the dimer about 50% of mice showed a pronounced accumulation of specific antibodies (FIG. 3a). The induced specific polyclonal immune response was measured in immunoblot. Recombinant murine PrP23-231 was separated on SDS-PAGE, transferred to PVDF membranes and incubated in an immunoblot analysis with serial dilutions of sera of immunized mice (primary antibody). The pre-immune sera were used to eliminate background signals. Staining was accomplished using conjugated secondary antibodies (anti-mouse) and the enhanced chemiluminescence kit (ECL plus, Amersham Corp., Buckinghamshire, U.K.). The mice immunized with PrP dimer showed higher antibody titers. Dilutions beyond 1:3000 still resulted in detectable signals. This finding indicates that the used immunogen was capable of overcoming the auto-tolerance phenomenon known for species-identical prion proteins. Further data showed that the induced antibodies were not directed against the N-terminal fusion domain or the linker sequence being reactive against authentic murine PrP23-231.

Figure 3B:
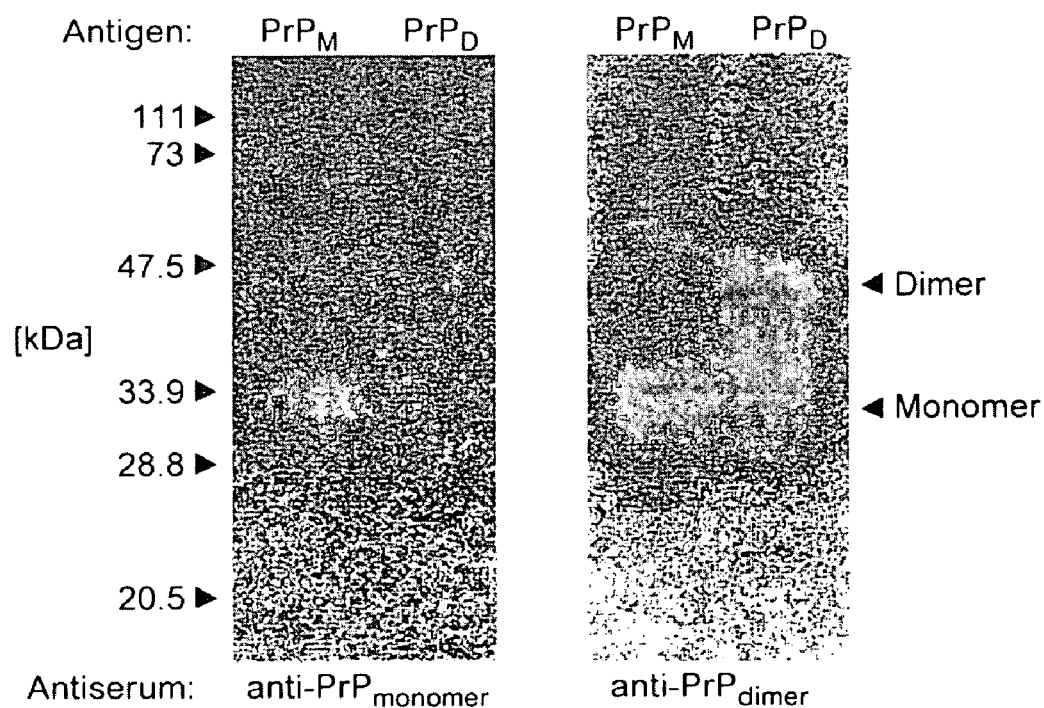

A similar result could already be achieved using rabbits, i.e. the rabbits immunized with the prion protein dimer showed a stronger immune response compared to the rabbits immunized with the prion protein monomer (FIG. 3b). Recombinant monomeric and dimeric prion proteins (PrPM and PrPD, respectively, which were used also as immunogens in immunization) were separated on SDS-PAGE, transferred to PVDF membranes and analyzed in immunoblot. The left panel shows incubation with the serum from the rabbit immunized with PrP monomer, the right panel from the arbbit immunized with PrP dimer. Staining was accomplished using conjugated anti-rabbit secondary antibodies and the ECL plus kit. Whereas the left panel shows mainly a reaction against the monomeric PrP, the right panel demonstrates a much stronger immune reactivity which is directed against monomeric and dimeric prion protein.

EXAMPLE 3

The Application of Antibodies Generated by Immunization with a prion protein dimer Leads to Inhibition of the de novo Synthesis of $PrP^{Sc}$ in vitro The biological relevance of the immunization experiments described in Example 2 could be verified by the following in vitro experiment. ScMHM2 cells [cultured murine neuroblastoma cells (ATCC CCL 131); persistently infected with RML prions; stably transfected with a 3F4-tagged PrP; c.f. Schätzl et al., J. Virol. 71, 8821-8831, (1997)] which are infected with the infectious version of the prion protein ($PrP^{Sc}$) and permanently produce $PrP^{Sc}$ were incubated with different types of antibodies. Incubation was carried using (a) commercially available monoclonal antibodies (3F4) (Signet Pathology Systems, Dedham, Mass., USA) which are directed against an epitope of the prion protein produced in ScMHM2 cells and (b) the antiserum obtained from rabbits immunized with the prion protein dimer described in Example 1. During incubation with antibodies for 16 hours proteins were metabolically labeled using $^{35}$S-methionine and subsequently immunoprecipitated (RIPA). Prior to the RIPA the cell lysates were separated into two fractions for digestion with proteinase K (+/−) and separated into soluble and insoluble fractions using ultra-centrifugation (1 hour, 100,000×g, 1% sarcosyl). As shown in FIG. 4, after incubation with the prion protein dimer for 16 hours a drastic inhibition of the de novo synthesis of PrP$^{Sc}$ could be observed. The results observed with the 3FA antibody are less pronounced. It can be concluded that this result is due to generation of a functional PrP$^c$ knock out state on the cell surface and, accordingly, an inhibition of the generation of PrP$^{Sc}$. These results demonstrate in living cells that the induced anti-PrP antibodies are capable of binding to surface-located authentic PrP$^c$ under native conditions (proof of principle for interaction with surface-located PrP under native conditions). Even more, bound antibodies are apparently internalised with PrP$^c$ demonstrating a high binding affinity (resulting in an insoluble PrP of full length which is PK sensitive, see full-length signal in FIG. 4A, lanes 5-8). Finally, endogeneous PrP$^{Sc}$ biogenesis was heavily impaired resulting in no more de novo generated PK resistant PrP$^{Sc}$ (FIG. 4B, lanes 7 and 8). The biological effect on PrP$^{Sc}$ biogenesis is therefore demonstrated as well (proof of principle for impairment of prion biogenesis). The efficiency of this principle could also be shown by using particular chemical compounds: The functional removal of surface-PrP$^c$ resulted in a reduction of the production of prion proteins.

---

The invention claimed is:

1. A prion protein dimer, wherein the prion protein dimer is a homodimer comprising two prion protein monomers derived from the same species or a heterodimer comprising two prion protein monomers derived from different species, wherein the prion protein dimer is a fusion protein, and wherein each of the prion protein monomers comprise a full-length prion protein monomer or a truncated prion protein monomer having at least 20 amino acids thereof.

2. The prion protein dimer of claim 1, wherein the prion protein monomers of the fusion protein are linked via a peptide spacer.

3. The prion protein dimer of claim 2, wherein the peptide spacer is (a) a spacer having a length of 2-3 amino acids, wherein the DNA sequence encoding the spacer contains a restriction site, (b) an oligomer composed of small neutral amino acids, or (c) an oligomer having an amino acid sequence that defines an epitope.

4. A prion protein dimer, wherein the prion protein dimer is a homodimer comprising two prion protein monomers derived from the same species or a heterodimer comprising two prion protein monomers derived from different species, wherein each of the prion protein monomers comprise a full-length prion protein monomer or a truncated prion protein monomer having at least 20 amino acids thereof and wherein the prion protein monomers are covalently coupled via polyethyleneglycol, activated benzodiazepine, oxazolone, azalactone, diketopiperazine or a monosaccharide.

5. The prion protein dimer of claim 1, wherein each of the prion protein monomers comprise a native full-length prion protein monomer or an N-terminally and/or C-terminally truncated prion protein monomer having at least 20 amino acids thereof.

6. A immunogenic composition comprising (i) a covalently coupled prion protein dimer, wherein the prion protein dimer is a homodimer comprising two prion protein monomers derived from the same species or a heterodimer comprising two prion protein monomers derived from different species, wherein each of the prion protein monomers comprise a native full-length prion protein monomer; (ii) an adjuvant; and (iii) a pharmaceutically acceptable carrier therefor.

7. The composition of claim 6, wherein the prion protein dimer is purified.

8. The composition of claim 6, wherein the prion protein dimer is a homodimer comprising two native full-length prion protein monomers.

9. The prion protein dimer of claim 1, wherein the prion protein dimer is a homodimer comprising two native full-length prion protein monomers.

10. The composition of claim 6, wherein the prion protein dimer is a fusion protein.

* * * * *